United States Patent [19]

Clifford

[11] Patent Number: 4,542,640

[45] Date of Patent: Sep. 24, 1985

[54] SELECTIVE GAS DETECTION AND MEASUREMENT SYSTEM

[76] Inventor: Paul K. Clifford, 590 Military Way, Palo Alto, Calif. 94306

[21] Appl. No.: 532,651

[22] Filed: Sep. 15, 1983

[51] Int. Cl.⁴ ............................................ G01N 27/12
[52] U.S. Cl. ...................................................... 73/23
[58] Field of Search ................. 73/23, 27 R; 324/71.5; 340/632, 633, 634; 422/98

[56] References Cited

U.S. PATENT DOCUMENTS

| | | | |
|---|---|---|---|
| 4,164,862 | 8/1979 | Jackson | 73/27 R |
| 4,432,224 | 2/1984 | Typpo | 73/23 |
| 4,443,791 | 4/1984 | Risgin et al. | 73/23 |
| 4,457,161 | 7/1984 | Iwanaga et al. | 73/23 |

OTHER PUBLICATIONS

"Research Progresses Toward a Selective MOS Gas Sensor", Paul K. Clifford, et al., Industrial Research & Development, Apr. 1982, pp. 143-148.

*Primary Examiner*—Stephen A. Kreitman
*Attorney, Agent, or Firm*—Thomas F. Meagher

[57] ABSTRACT

A gas detecting system for determining the presence and concentrations of a number of selected toxic, combustible, or reducing gases in an atmosphere. The system includes a plurality of semiconductor gas sensors, each of which differs from each of the others in its response to at least one of the selected gases. The system includes a means of processing the responses of each sensor to produce an indication of each of the gas concentrations. The system may also produce indications of the measurement accuracy of each gas concentration, which can be used to determine the presence of gases not selected for detection.

16 Claims, 1 Drawing Figure

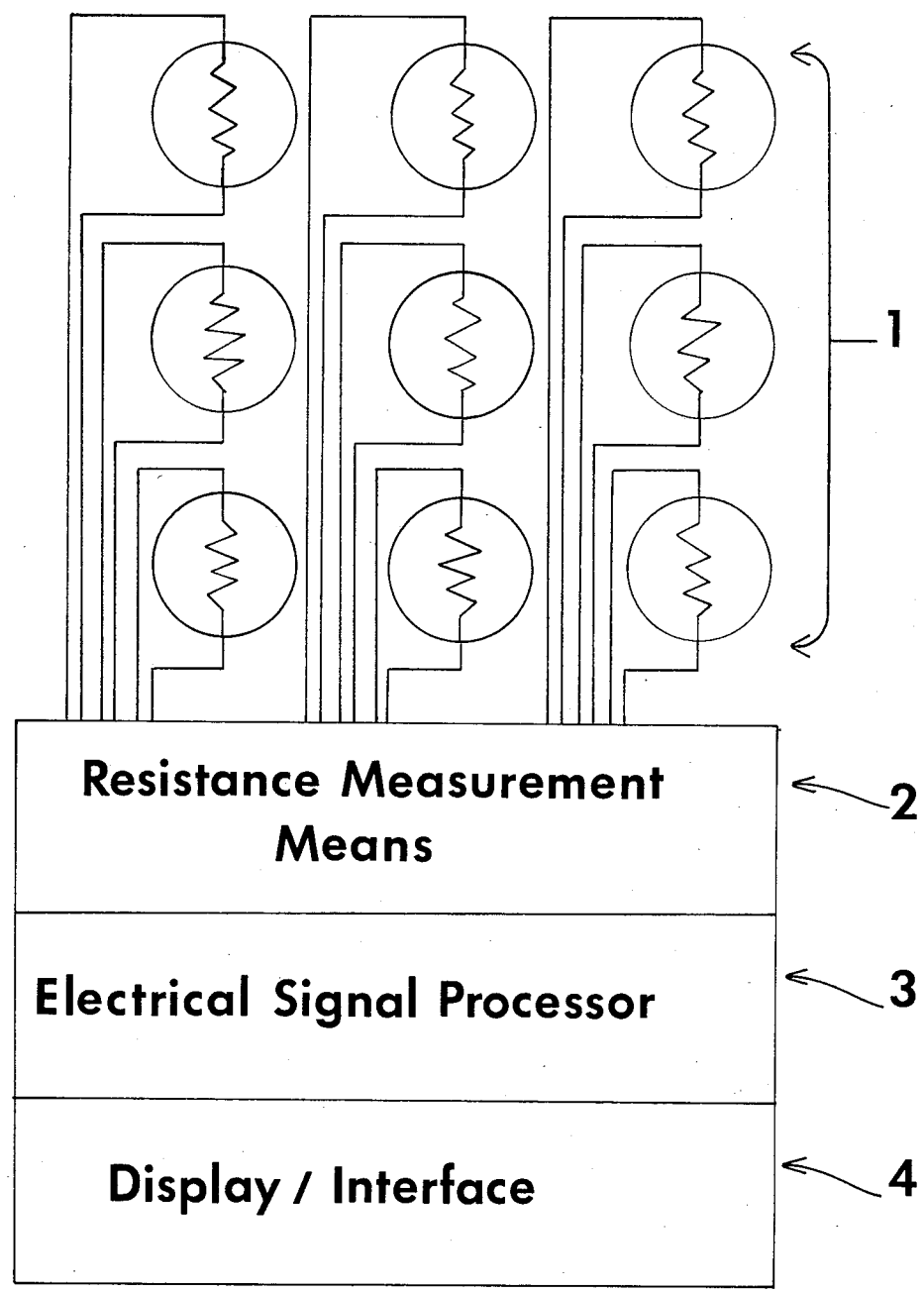

SELECTIVE GAS DETECTION AND MEASUREMENT SYSTEM

The invention relates generally to a system for qualitatively and quantitatively detecting and identifying gases, and more particularly to such as system which uses semiconductor gas sensors to detect toxic, combustible, or reducing gases.

Homogeneous semiconductor gas sensors (that is, unstructured gas sensors as defined by G. Heiland in "Homogeneous Semiconductor Gas Sensors", Sensors and Actuators, Vol. 2, 1982, pp. 343-361) are small, rugged, and chemically inert. Owing to these advantages, they seem ideally suited to the development of portable and inexpensive chemical sensors.

Homogeneous semiconductor gas sensors are used to detect polluting, toxic, and combustible gases such as carbon monoxide, hydrocarbons, hydrogen, acetone, ammonia, hydrogen sulfide, alcohol vapors, solvent vapors, and many other gases. (The polluting, toxic, and combustible gases are hereafter often referred to simply as "gases" or "gaseous constituents". It should be understood that whenever these terms are used, it is meant that these gases occur as impurities in an air atmosphere.) These semiconductor sensors are generally composed of bulk n-type metal oxides such as tin oxide, zinc oxide, and ferric sesquioxide, but p-type metal oxides may also be used, as well as semiconductor materials which are not composed of metal oxides. The Taguchi Gas Sensor (TGS, U.S. Pat. Nos. 3,676,820, 3,695,848, 3,900,815) provides representative teachings in the art. Its properties are typical of those of most homogeneous semiconductor gas sensors. It is sensitive to combustible gases with detection thresholds to hydrogen, carbon monoxide, and ethanol gases in the part per million (ppm) range. These gas sensors adsorb reducing or combustible gases such as hydrocarbons, hydrogen, carbon monoxide, water, methane, alcohols, smoke, and others and convert the concentrations of gases into an electrical signal by changing resistivity. Although particular reference is made herein to the Taguchi Gas Sensor, equivalent solid state or semiconductor sensors of the homogeneous variety may be used. These include single crystal or polycrystalline semiconductors of the bulk or thin film type, amorphous semiconducting materials, metal oxide ceramics, composite materials of metal oxides, sulfates, and nonmetal oxides, organic semiconductor materials, and others.

Homogeneous semiconductor sensors, while sensitive to combustible or reducing gases at the parts per million level, are limited by their response nonlinearity and their lack of selectivity. From a practical standpoint, a gas sensor is useful only if it can detect the desired gas in the presence of background constituents. As a result, their primary applications have been limited to smoke detection, not for gas identification or gas sensing at low concentrations.

The greatest limitation of these sensors is that they respond to a greater or lesser extent to many reducing gases, so that present measuring systems equipped with these sensors can only be used for determining the cumulative effect of the combustible gas components in a mixture of gases, and cannot be used to distinguish one gas from another. They respond to many gases by changing resistance or resistivity. Because accurate models of the sensor's resistance response and means to employ such a model have not been available, it has not been possible to quantitatively determine the concentration of a single gas if a sensor is simultaneously exposed to several gases to which it is sensitive.

In addition, when exposed to an atmosphere which in addition to the gas or gases selected for detection also contains a particular constituent which causes interference, prior art sensors produce erroneous results and provide no indication that an error has occurred.

An essential feature of a homogeneous semiconductor gas sensor is its nonlinear response. For a limited range of gas concentration the relationship between steady state sensor resistance, R, and a single gas concentration in air, [G], is given by, $$R = \alpha [G]^{-\beta} \tag{1}$$

in which $\alpha$ and $\beta$ are constants at constant sensor temperature. This nonlinear response characteristic can be accommodated by straightforward signal processing or the display of results using nonlinear scales. Direct reading instruments based on available sensors, for example the TGS, use nonlinear scales, and are suitable for detection in an atmosphere containing only one gas. It is possible to use analog electrical processing of the signal from such a sensor to linearize the output as is taught by U.S. Pat. No. 4,351,181 (Currans). Such a procedure can be used only if a single gas to which the sensor is responsive is present. Two or more gases cause erroneous readings. However, in the more common situation in which a plurality of gas constituents are present, formulas of the type of Eq. (1) are inadequate. Prior to the present invention, an adequate representation of the sensor response to a plurality of gases did not exist; consequently appropriate signal processing to linearize the sensor response was not possible.

Because their intrinsic unselectivity constitutes a serious impediment to the use of homogeneous semiconductor gas sensors, much effort has been devoted to improving selectivity. Efforts have concentrated on filtering or variations of sensor composition, doping, or surface preparation with a view to producing sensitivity to only a single gas. These efforts have been partially successful, achieving greater response to one gas or another, but not achieving selectivity. These efforts have included:

1. Covering the sensor with a dielectric film to enhance selectivity to smoke as taught by U.S. Pat. No. 4,016,524 (Pompei et al).
2. Combining homogeneous semiconductor gas sensors with membranes. Selective membranes have been combined with the Taguchi Gas Sensor for example as taught by U.S. Pat. No. 3,864,628 (Klass et al) and U.S. Pat. No. 4,256,985 (Goodson et al) and the responses of two sensors compared by electrical means in order to reduce the sensitivity of the sensor system to a particular interference gas.
3. Using a plurality of sensing elements, each of which has a different sensitivity for at least one of the gaseous components to be detected. These attempts have been unsuccessful owing to the lack of a response model for the homogeneous semiconductor gas sensors which accounts for the combined effects of a number of gases. The relationships between the resistance (or equivalently current or voltage) responses of the individual sensors and the gaseous components were not known sufficiently in order to process the response signals and thereby to transform them into representations of the gas concentrations or types. These attempts have included:

a. An array of homogeneous semiconductor gas sensors which are composed of organic semiconductor materials as taught by U.S. Pat. No. 3,428,892 (Meinhard).
b. An array of field effect transistors with different response characteristics by virtue of having chemically specific films in the gate region as taught in U.S. Pat. No. 3,831,432 (Cox).
c. A combination of sensors with different response characteristics as taught by U.S. Pat. No. 3,961,248 (Kawamura). This system is capable of qualitative identification of the gas present, but works only if just one of two selected gases is present.

None of these prior art inventions provides a model which quantitatively relates the resistances of the sensors to the constituent gas concentrations or a means of processing the signals from the array of sensors to determine the individual gas concentrations.

4. Monitoring reaction speed to distinguish carbon monoxide from hydrocarbons as taught in U.S. Pat. No. 4,012,692 (Eicker).
5. Applying filters to homogeneous semiconductor gas sensors or preconditioning the gas stream to be sensed. Molecular sieves have been applied to an array of homogeneous semiconductor gas sensors for better selectivity as taught in U.S. Pat. No. 4,347,732 (Leary).

Each of these efforts have proven inadequate, and do not result in selectivity to particular gases, nor immunity to interference gases.

Accordingly it is an object of the invention to provide a selective gas detection system. Such a system is needed to meet the requirements for indoor air quality monitoring and to detect or measure gases such as methane, carbon monoxide, hydrogen, ethanol, hydrogen sulfide, and solvent vapors.

Briefly, in accordance with the principles of the invention, the gas detection system includes a plurality (hereafter called an array) of sensors which may consist of any type or combination of types of prior art homogeneous semiconductor gas sensors, either separately constructed or fabricated on a single substrate, or microfabricated using semiconductor fabrication technology. The number of individual sensors in the array is greater than or equal to the number of selected gases to be distinguished. Each sensor of the array should have a response characteristic which differs from the response characteristics of each of the other sensors in the array in its response to at least one of the set of selected gases. This difference may result from the sensor's composition, operating temperature, material preparation, surface modification, or any combination of these, or by virtue of its exposure to a prefiltered gas stream.

Before use in the detection system the resistance responses of each sensor of the array to each of the selected gases and to combinations of the selected gases are precisely measured. These measurements are used to determine values of constants in specific equations, each of which is in the form of the general response equation herein disclosed.

The system combines the array with a means of measuring resistances (or equivalently conductances, voltages, or currents), a means of converting those measurements into electrical signals (hereafter called sensor signals), and a means of applying those signals to an electrical processor. The electrical processor, through analog or digital processing, or some combination of each, performs pattern recognition logic operations capable of giving prompt display of gas constituents encountered by the array. In the preferred embodiment the pattern recognition logic operations are accomplished by a digital processor which performs mathematical operations to process the sensor signals. It does this by solving a particular system of equations, herein disclosed, one equation for each sensor of the array. The purpose of this signal processing is to to transform the electrical signals representing sensor resistances into electrical signals representing individual gas concentrations. This information is then indicated using meters, displays, printers or any electrical means. In addition, information representing the accuracy of the gas concentration determinations may be generated and indicated. For an array consisting of only a small number of sensors the electrical processing may be accomplished by analog circuitry.

FIG. 1 illustrates, partially schematically and partially by block diagram, a gas detection system embodying the principles of the invention.

This invention makes use of a response model for homogeneous semiconductor gas sensors which describes the causes of their poor selectivity, quantifies their response to combinations of gases, and provides detailed understanding of the interactions between various gases. This quantitative model of device operation unifies the diverse properties of the TGS and other semiconductor sensors. The model supplies the mathematical framework for meaningful quantitative comparisons of sensor performances and gas sensitivities. In addition, it provides for the competitive and associative interactions of several gases detected simultaneously, and the source of individual sensor unselectivity.

The functional dependence of sensor response on individual gas concentrations is described by a general response equation which identifies the causes of sensor unselectivity. It reveals that from a single response measurement it is impossible to deduce the number, type, or concentrations of the ambient gases which contribute to the response. The general response equation provides the precise extent of a sensor's resistance response to a plurality of ambient gas concentrations. The steady state resistance, R, of any homogeneous semiconductor gas sensor to several gases in air is expressed by, $$F(R) = 1 + \sum_{i=1}^{L} \left( K_i \prod_{j=1}^{M} [G_j]^{n_{ij}} \right) \quad (2)$$

in which F(R) indicates a known and previously measured function of sensor resistance R, j is a counter which indicates the gas type, M is the total number of reducing or combustible gases in the atmosphere, $[G_j]$ represent reducing or combustible gas concentrations, $n_{ij}$ are numerical constants, and i is a counter which distinguishes individual terms in the summation of Eq. (2). The $\Sigma$ symbol represents a summation, and the $\pi$ symbol represents a product. Each term of the summation itself includes a product of gas concentrations. In general, for a particular gas sensor's response, each term of the summation need not necessarily contain the product of all gas concentrations because many of the fixed powers, $n_{ij}$, are frequently zero.

F(R) is a function which is independent of the gas concentrations; that is, the role of gases in Eq. (2) is completely and explicitly shown on the right side of the equation. F(R) is hereafter termed the resistance function. It depends on sensor operating temperature, oxygen partial pressure and sensor composition. Consequently, for a particular sensor operated in an air atmosphere at constant operating temperature, F(R) is a well known function of sensor resistance. For many homogeneous semiconductor gas sensors F(R) is a power law function of sensor resistance.

The $K_i$ of Eq. (2) are hereafter referred to as "gas sensitivity coefficients". They are numerical constants for a sensor operated at fixed temperature in an air atmosphere.

This equation, Eq. (2), accurately describes the nonlinear response of any homogeneous semiconducting gas sensor to a multiplicity of gaseous constituents. Appropriate limiting forms of Eq. (2) are used to model the resistance response of any particular homogeneous semiconductor gas sensor to any number of combustible or reducing gases in air. What distinguishes the response of one sensor from that of another is the form of its resistance function, the values of its $n_{ij}$ (hereafter referred to as "powers"), and the values of its gas sensitivity coefficients in the response equation. For example, an appropriate form of the equation completely describes the steady state resistance response of a commercially available gas sensor to several combustible and reducing gases. The steady state resistance response of that sensor to any combination of methane, water vapor, hydrogen, and carbon monoxide gases in air is given by, $$F(R) = 1 + K_1[CH_4] + K_2[H_2O] + K_3[H_2]^2 + K_4[H_2O][CO] + K_5[H_2O][CO]^2 \quad (3)$$

This equation is generated from Eq. (2) by having $G_1$, $G_2$, $G_3$, and $G_4$ represented by methane ($CH_4$), water vapor ($H_2O$), hydrogen ($H_2$), and carbon monoxide (CO) respectively. In the equation, $n_{11} = n_{22} = n_{42} = n_{44} = n_{52} = 1$, $n_{33} = n_{54} = 2$ and all other $n_{ij} = 0$. $K_1$, $K_2$, $K_3$, $K_4$ and $K_5$ are numerical constants. The total number of terms in the summation is $L = 5$ and the number of selected gases is $M = 4$. For this sensor operated in an air atmosphere, the resistance function of Eq. (3) is given by, $$F(R) = (R/R_o)^{-1/\beta} \quad (4)$$

in which R represents sensor resistance, $R_o$ indicates the sensor resistance in pure air, that is, when no combustible or reducing gases are present, and $\beta$ is a constant at constant sensor temperature.

The response equation, Eq. (2), provides cogent mathematical description of the nonlinear influence of a multiplicity of gaseous components on a sensor's resistance, including competitive and associative interactions that have previously only been qualitatively described. Because the resistance response of a sensor depends on a summation of terms, the effects of one gas can be masked by the combined effects of others. A single term's influence cannot be discerned until its contribution to the sum of Eq. (2) becomes significant. In addition to this competitive effect there is an associative interaction by which the effects of one gas are enhanced by the presence of another. This occurs when the product of several gas concentrations constitutes a single term in the sum, for instance the [CO][$H_2O$] term of Eq. (3).

Using this response model it is not necessary that each sensor have absolute selectivity to a single gas. The functional dependence of sensor response on individual gas concentrations and products of gas concentrations is used to transform the electrical signals from several homogeneous semiconductor gas sensing devices into signals which represent the gas concentrations. Signal processing methods which rely only on a sensor's differing relative sensitivities to different gases are used to decipher the complex responses of a number of different sensors and thereby to determine constituent gas concentrations. The response model of Eq. (2) provides the framework necessary for the development of selective multi-sensor gas detection systems. The combination of an array of several intrinsically unselective gas sensors and an electrical processor provides sensitive and selective detection, as well as identification of many gases simultaneously.

In FIG. 1, an illustrative embodiment of the invention is shown. An array of precalibrated semiconductor gas sensors is coupled to a processing unit which measures sensor resistances and transforms signals representing the resistances into signals representing individual gas concentrations.

In any given application there are some number, M, of selected gases to be monitored. These gases should include not only the hazardous, polluting, combustible or toxic gases targeted for measurement but also any other interference gases or other impurities likely to be encountered by the detection instrument. An array of sensors is constructed which consists of some number of sensors, N, where N is greater than or equal to M. The array (or an identical array) is calibrated by a method to be described.

The gas detection system of FIG. 1 consists primarily of this array 1, a means 2 of measuring the resistances of the sensors of the array, an electrical processing unit 3 and a display or signal interface 4. For each gas sensing element of the array (for instance the k-th sensor) there is a response equation of the form of Eq. (2), represented in (or accessible to) the processing unit by prerecorded values for the resistance function, $F_k(R_k)$, the gas sensitivity coefficients, $K_{ki}$, and the powers, $n_{ij}$.

Ideally, each of the sensors in a gas detection system should be as sensitive as possible to a single gas and unresponsive to other atmospheric constituents. However, that degree of selectivity is not essential. Nevertheless, the sensors should satisfy the following conditions:

1. Any individual sensor in the array differs from each of the other sensors of the array in its response to at least one gas or class of gases in the set of selected gases,
2. The responses of each sensor to all of the selected gases are known, and,
3. The number of sensors equals or exceeds the total number of selected gases to be monitored; that is, $N > M$.

Total selectivity is not necessary, but the individual sensors must be reproducible and their responses must be characterized by Eq. (2). If this is so, the discrimination of gases and the determinations of gas concentrations are accomplished by electrically processing the sensor resistance signals.

In this approach, absolute selectivity for a given gas is not expected of a single sensor. An array of sensors is used, each sensor of which satisfies the basic requirements of sensitivity, and each of which differs from each of the other members in its response to at least one gas of interest. This difference is manifest in differences in the sensors' gas sensitivity coefficients or in their powers. Each member of the array is then characterized to the degree necessary for unambiguous reduction of the response equations.

Many different types of prior art sensors may be used in this invention, thereby greatly expanding their utility. The sensor array can be composed of, but not limited to, any of the following types of homogeneous semiconductor gas sensors. The responses of each of these types of sensor can be well characterized by Eq. (2):

1. Both n-type and p-type semiconductor gas sensors.
2. Semiconductor gas detectors of the unstructured type as described by Heiland.
3. Metal oxide sensors such as the Taguchi Gas Sensor as described in U.S. Pat. No. 3,625,756 (Taguchi), U.S.. Pat. No. 3,631,436 (Taguchi), U.S. Pat. No. 3,644,795 (Taguchi), U.S. Pat. No. 3,676,820 (Taguchi), U.S. Pat. No. 3,695,848 (Taguchi), U.S. Pat. No. 3,732,519 (Taguchi), U.S. Pat. No. 3,835,529 (Taguchi), and U.S. Pat. No. 3,900,815 (Taguchi).
4. Semiconductor sensors containing electron transfer additives on the surface as described in U.S. Pat. No. 4,039,941 (Morrison).
5. Solid state electrochemical cells used for gas detection for example as described in U.S. Pat. No. 3,955,268 (Chou) and U.S. Pat. No. 4,013,943 (Chou).
6. Multifunction ceramic gas sensors of the type described in U.S. Pat. No. 4,378,691 (Terada et al).
7. Variously doped tin oxide sensors including those described by U.S. Pat. No. 3,901,067 (Boardman) and U.S. Pat. No. 3,955,929 (Kawakami et al).
8. Organic semiconductor gas sensors for example as described by U.S. Pat. No. 3,428,892 (Meinhard), U.S. Pat. No. 4,381,922 (Frey), U.S. Pat. No. 3,645,999 (Byrd), and U.S. Pat. No. 4,350,660 (Robinson).
9. Sensors composed of oxyacid salt semiconductors as described by U.S. Pat. No. 4,067,695 (Miyaguchi).
10. Sensors prepared from polymer gels for example as taught by U.S. Pat. No. 4,266,978 (Prochazka).
11. Single crystal gas sensors such as those of zinc oxide described by U.S. Pat. No. 4,198,850.
12. Perovskite structure metal oxides for example as taught by U.S. Pat. No. 4,221,827 (Parry), U.S. Pat. No. 4,044,601 (Sakurai et al), or U.S. Pat. No. 3,951,603 (Obayashi).
13. Complex metal oxides for example as taught by U.S. Pat. No. 3,953,173 (Obayashi et al).
14. Semiconductor humidity sensors of the types described in U.S. Pat. No. 4,050,048 (Frazee), U.S. Pat. No. 4,015,230 (Nitta et al), U.S. Pat. No. 4,378,691 (Terada et al), U.S. Pat. No. 3,748,625 (Bennewitz), or U.S. Pat. No. 4,086,556 (Nitta et al).

In addition to these prior art sensors, new sensor materials can be constructed; the fundamental requirement is that the individual sensors of the array have different sensitivities to the selected gases. In general, semiconductor materials which catalyze the oxidation of the gases of interest are good candidates for the sensing material.

The pertinent catalytic literature and the gas sensing art teaches that many materials of various compositions can be used. These include metal oxides which act as catalysts for the oxidation of combustible or reducing gases and which also exhibit either n-type or p-type semiconductivity. They include but are not limited to $SnO_2$, $ZnO$, $CdO$, $PbCrO_4$, $Fe_2O_3$, $TiO_2$, $ThO_2$, $MoO_3$, $V_2O_5$, $MnO_2$, $WO_3$, $NiO$, $CoO$, $Cr_2O_3$, $Ag_2O$, and $In_2O_3$. Sensors composed of these materials conform to the response equation, Eq. (2). In addition p-type metal oxides are also described by the response equation and can likewise be used to construct the sensor array of this invention. Metal oxides having perovskite crystal structures are also such catalysts and can be used.

Differing relative gas sensitivities can be created by addition of certain metals, "activators", to the bulk composition or to the surface of homogeneous semiconductor gas sensors. Such addition enhances the oxidation of particular gases over metal oxides and results in a greater response to those gases. Platinum is used to activate the oxides of molybdenum, chromium, titanium, iron, niobium, and nickel. On tungsten oxide, besides platinum, such activators include surface monolayer amounts of iridium, rhodium, gold, and palladium. On tin oxide, gold or gold oxide enhances the response to butane for example as taught by U.S. Pat. No. 3,676,820 (Taguchi).

Tungsten oxide films may be doped with platinum catalyst to enhance detection of ammonia over that of hydrogen, and tungsten trioxide can be used to enhance detection of hydrogen sulfide for example as taught by U.S. Pat. No. 4,197,089 (Willis et al). Mixed metal oxide films can be covered with discontinuous layers of catalysts to gain greater sensitivities to particular gases for example as taught by U.S. Pat. No. 3,479,257 (Shaver). Palladium films can be deposited on stannic oxide to enhance the sensitivity to hydrogen for example as taught by U.S. Pat. No. 4,030,340 (Chang) or doped to enhance the sensitivity to hydrogen sulfide for example as taught by U.S. Pat. No. 3,901,067 (Boardman, Jr. et al).

Relative sensitivites to gases can also be modified by variations of bulk composition and/or doping. The relative sensitivities of an $SnO_2$ based device, similar in composition to the TGS to CO, $H_2$, and hydrocarbons can be reproducibly modified by alteration of composition with other metal oxides ($ThO_2$, $Sb_2O_5$, silica, $MgO$) or by doping with transition metals (Nb, V, Ti, or Mo). In addition the catalyst Pd can be added as $PdCl_2$ to catalyze the detection of $H_2$, CO and iso-$C_4H_{10}$ equally, or $ThO_2$ and silica added to preferentially enhance the sensitivity to CO over those of hydrocarbons. Devices composed of other metal oxides, for example $V_2O_5$ or $Fe_2O_3$ exhibit similar behavior and their sensitivities can also be modified by appropriate doping. Additionally, the catalytic literature is rich with oxidation catalysts with different activities for different gases.

Differences in sensitivities to particular gases can also be created by manipulating sensor operating temperature. The measured responses of $SnO_2$ devices to $H_2$ and CO each exhibit characteristically different temperature dependences. In fact, with any doping combination sensitivities of $SnO_2$ gas sensors remain highly temperature dependent; this is true for most homogeneous semiconductor gas sensors. Consequently, otherwise identical sensors can be operated at different temperatures to achieve different gas sensitivity coefficients from one to another.

Filtering of the gas phase may be used to partially separate ambient gas constituents before exposure of the semiconductor surface. A semipermeable membrane or film interposed between the active surfaces of selected sensors and the source of ambient gas can admit certain molecular components of the ambient gases while excluding others. Although the separation is usually incomplete, a set of different filters or semipermeable membranes and identical sensors can be used to produce the sensor array.

Any of these techniques (choice of sensors of different compositions, temperature variation, combination with selective or semipermeable membranes, and preprocessing or filtering of the ambient gas) can be used to construct an array of sensors of differing sensitivities. These techniques can be applied separately or in any combination.

Sensors of the array can be sintered, chemically deposited, prepared from polymer gels for example as taught by U.S. Pat. No. 4,266,978 (Prochazka), screen printed, or otherwise fabricated. Sensors can be polycrystalline or single crystals. Sensors can be fabricated on a single substrate or separately. Individual sensors can share a common heating means, or if different sensor operating temperatures are desired, heating means may be separate.

For a particular sensor the most significant terms of Eq. (2) are found by straightforward measurement of the resistance response of the sensor to individual combustible or reducing gas concentrations, and to combinations of gas concentrations. Each sensor of the array is calibrated by precisely measuring its resistance response to known concentrations of the selected gases produced by diluting samples of the selected gases in a standard ambient gas, usually air. It is not necessary to have knowledge of the catalytic nature of the individual sensors, provided that sufficient reference samples are used to determine the parameters of the model. These parameters consist of the resistance function, the gas sensitivity coefficients, and the powers.

Each sensor's steady state resistance is measured as a function of each of the selected gas's concentration. This is done for a great range of gas concentrations, extending from less than the detectable limit to more than the greatest gas concentration to which it is expected that the sensor will be exposed in use. The resistance measurements and the known gas concentrations are curve fitted to the model equation, Eq. (2), to obtain numerical values of the pertinent gas sensitivity coefficients, the powers, and the resistance function. After this is done for each gas separately, it is then done for various combinations of gases. This procedure has been used to determine the terms of the equation which are of practical importance for a commercially available gas sensor (see Paul K. Clifford and D. T. Tuma, "Characteristics of Semiconductor Gas Sensors: I Steady State Gas Response", Sensors and Actuators, Vol. 3(3), 1983, pp. 233–254). For that sensor this calibration procedure results in the response indicated in Eq. (3).

A means is employed within the gas detection system for measuring the resistances of the individual homogeneous semiconductor gas sensors which compose the sensor array. Conductance, voltage, or current measurements can be used instead of resistance measurements.

The array of sensors are represented within an electrical processor, or accessible to it, by a system of response equations, each equation patterned after Eq. (2). These equations may be represented in a great variety of ways: as electrical signals, as numerical constants representing the resistance functions, gas sensitivity coefficients and powers stored in an electrical or magnetic memory, as voltages, or as values of electrical components, among others. Whatever the representation, these equations are used by the electrical processor to transform the sensor signals into signals representing gas concentrations.

Just as it is always possible to represent the response of any particular homogeneous semiconductor gas sensor with Eq. (2), the N responses of a collection of N homogeneous semiconductor gas sensors can be represented by a system of equations, each patterned on Eq. (2). There are M gases of interest, which combine in the equations to produce a total, among all the responsed equations, of L different gas terms. For convenience in notation each equation is shown containing all L terms in the summation, even though in practice, many of the $K_{ki}$ may be zero:

1'st sensor:
$$F_1(R_1) = 1 + \sum_{i=1}^{L} \left( K_{1i} \prod_{j=1}^{M} [G_j]^{n_{ij}} \right) + \epsilon_1 \quad (5)$$

2'nd sensor:
$$F_2(R_2) = 1 + \sum_{i=1}^{L} \left( K_{2i} \prod_{j=1}^{M} [G_j]^{n_{ij}} \right) + \epsilon_2$$

...

$k$'th sensor:
$$F_k(R_k) = 1 + \sum_{i=1}^{L} \left( K_{ki} \prod_{j=1}^{M} [G_j]^{n_{ij}} \right) + \epsilon_k$$

...

$N$'th sensor:
$$F_N(R_N) = 1 + \sum_{i=1}^{L} \left( K_{Ni} \prod_{j=1}^{M} [G_j]^{n_{ij}} \right) + \epsilon_N$$

in which the $F_k(R_k)$ are known and previously determined functions for each sensor of that sensor's measured resistance, $R_k$, and the $\epsilon_k$ are error terms discussed below.

In practice for many terms of the summation in the equations above, most of the $n_{ij}$ are zero. In other words, most terms in the summation often contain only one gas concentration; the other concentrations in the term, because their exponents are zero, are equivalent to unity. Some terms however will contain a product of several gas concentrations, as is the case for the $[H_2O][CO]$ and $[H_2O][CO]^2$ terms in Eq. (3).

The pertinent art contains many signal processing techniques, computational techniques, or numerical methods by which the independent gas terms of the system of equations can be determined. The availability of small, powerful electrical microprocessors allows even very large systems of nonlinear equations such as these to be solved in a time shorter than, or comparable to, the response times of the individual sensors. In other applications requiring selective detection of only one or two gases the system of equations can be very simple, containing only several terms, and can be solved using analog signal processing or digital logic.

For many applications, the gas sensitivity coefficients and the powers in the system of equations will be such that the system is a linear system. In that case, if N is not less than L, a least squared processing technique as taught by standard references (see for example N. R. Draper and H. Smith, *Applied Regression Analysis*, John Wiley & Sons, Inc., New York, Second Edition, 1966, or, G. Dahlquist and Ake Bjorg, Numerical Methods, Prentice-Hall, Inc., Englewood Cliffs, N.J.) may be used to transform the sensor signals into gas concentration signals.

For other applications, the system may have many terms containing the product of several gas concentrations. For these nonlinear systems, nonlinear solution techniques such as the Gauss-Seidel iteration method, the Newton-Raphson method, and Steffensen's method can be used, and are taught in standard references.

Each equation of Eq. (5) represents the general response equation for M gas constituents, with the summation over all possible detection terms truncated to the L most influential terms. The terms required depend on the particular detection environment and the gases selected for detection. Truncation of the summation to a finite number of the L most important terms introduces small errors. These error terms, together with the errors associated with the resistance measurement, and the errors caused by approximating the response with Eq. (2) (that is, by neglecting time dependent terms) are represented in Eq. (5) by the $\epsilon_k$ and largely determine the detection accuracy. The influence of interference gases (that is, those gases to which the sensors are sensitive but which are not among the selected gases) in the atmosphere is to increase the value of the error terms, and ultimately to degrade the accuracy of the determination of the selected gas concentrations. The extent of that degradation is determined along with the selected gas concentrations by the electrical processor. The magnitudes of the error terms need not be known but can be estimated if desired by the same processing which is used to determine the gas concentrations.

If a sufficient number of sensors is chosen, standard signal processing techniques (such as least squared estimation) are used to transform the errors, $\epsilon_k$, into signals representing accuracies or estimates of the likelihood (or confidence) intervals for the gas concentration signals, designated $\pm \Delta G_j$. This is possible even if a nonlinear least squared solution technique is used. The benefit of this process is that the detection system determines not only the concentrations of the selected gases to which it is exposed, but it also determines the accuracies of those determinations.

Because unknown interference gases increase the error terms, their influence on the detection system's results is to increase the likelihood intervals for the gas concentrations. Consequently, if the gas detection system is placed in an ambient which contains a gas to which the semiconductor sensors are responsive, but which is not among the selected gases, it may then provide an indication of the magnitudes of the errors that the interfering gas causes to the determinations of the concentrations of the selected gases. These signals can be used to indicate the presence of interference gases.

In general, the greater the number of excess independent equations, N-M, the greater is the accuracy of the gas concentration determination. When N>M, processing can determine the gas concentrations, $[G_j]$, and the error bounds associated with each of the gas concentrations, $\pm \Delta G_j$.

The electrical processor may also be used to provide an indication or alarm signal whenever a particular gas concentration attains a specified value or whenever gas concentrations or combinations of gas concentrations exceed threshold values. It may also be used to provide an indication or display of gas concentrations or their measurement accuracies, or to transmit those values by electrical means to a display or other processor.

By application of standard engineering practice, the gas detection system herein described may be expanded to include a number of arrays of sensors, each in a different location (for example, in different rooms of a building), so that gas concentrations may be monitored or determined in a number of different locations. Separate electrical processors are not needed for each array of sensors; a single electrical processor is sufficient to transform the set of sensor signals derived from each array into sets of gas concentration signals for each location. The sets of gases selected for detection at each location need not be the same.

In addition to the above mentioned functions, the electrical processor, either alone or in conjunction with other electrical circuitry, may be used to control the temperatures of sensors which are electrically heated.

An an example of a detection system, consider the requirements of selectively detecting low concentrations (0–1000 ppm) of a carbon monoxide in the air in an environment that also contains methane. A single selective sensor suitable for the job is not available. However, highly sensitive sensors for carbon monoxide are commercially available which also have appreciable sensitivity to methane and water vapor. It is therefore necessary to use a sensor array which includes sensors of differing sensitivities to the three selected gases, CO, $CH_4$, and $H_2O$.

The sensor array chosen is composed of a commercially available gas sensor operated at a particular temperature, designated sensor 1; the same type of gas sensor operated at a second temperature, designated sensor 2; in addition to a different type of homogeneous semiconductor gas sensor which is more sensitive to methane than to carbon monoxide operated at its standard temperature, designated sensor 3; and a metal oxide humidity sensor which is sensitive only to water vapor, designated sensor 4. Each of the sensors is calibrated for all of the selected gases to obtain their resistance functions and numerical values for their gas sensitivity coefficients and powers. The sensors are represented by the system of equations:

Sensor 1:
$$(R_1/R_{10})^{-1/\beta_1} = 1 + K_{11}[CH_4] + K_{12}[H_2O] + K_{13}[H_2O][CO] \quad (6)$$

Sensor 2:
$$(R_2/R_{20})^{-1/\beta_2} = 1 + K_{21}[CH_4] + K_{22}[H_2O] + K_{23}[H_2O][CO]$$

Sensor 3:
$$(R_3/R_{30})^{-1/\beta_3} = 1 + K_{31}[CH_4] + K_{32}[H_2O] + K_{33}[H_2O][CO]$$

Sensor 4: $\alpha_1 \log(R_4/R_{40}) = 1 + K_{42}[H_2O]$ in which the constants are all determined from the calibration procedure. Terms for which the gas sensitivity coefficients are not appreciable ($K_{41}$ and $K_{43}$) are not needed. The detection system measures the four resistances of the sensors, $R_1$, $R_2$, $R_3$, and $R_4$. These resistance signals are then processed using Eq. (6) to obtain signals representing the individual gas concentrations, [CO], $[CH_4]$, and $[H_2O]$. In this case the equations are easily solved using a small microprocessor. Consequently, the entire instrument can be portable. Because the number of equations is greater than the number of gases to be determined, N>M, the detection accuracy for each of the gas concentrations is also determined using a least squares processing technique.

Since many changes can be made in the configuration as well as the applications of the invention, changes which will be obvious to those schooled in the art, my intent in the appended claims is to cover all such changes and modifications as fall within the spirit and scope of the invention.

What is claimed is:

1. A system for selectively detecting, measuring, and identifying a selected number of gases in an atmosphere comprising:

a plurality of semiconductor sensors, greater or equal in number to the number of selected gases, each with a predetermined response characteristic which differs from the response characteristic of each of the other sensors in its response to at least one of the set of selected gases;

means, coupled to each of said sensors, for deriving a plurality of electrical signals, each of said signals representing the response to said atmosphere of a respectively different one of said sensors; and electrical signal processing means, responsive to said plurality of derived signals, for developing respective indications of the concentrations of each of said selected gases as solutions of a set of equations, each of which is of the form $$F(R) = 1 + \sum_{i=1}^{L} \left( K_i \prod_{j=1}^{M} [G_j]^{n_{ij}} \right)$$

in which F(R) indicates a known and previously measured function of the response signal R of the particular sensor, j is a counter which indicates the gas type, M is the number of selected gases, $[G_j]$ represent the concentrations of the selected gases, $n_{ij}$ are numerical constants of the particular sensor, $\Sigma$ is the symbol representing summation, i is a counter which distinguishes individual terms in the summation, L is the total number of terms in the summation, $\pi$ is the symbol representing products, and the $K_i$ are previously measured numerical constants of the particular sensor.

2. The system of claim 1, wherein said electrical signal processing means includes means for determining the errors associated with each gas concentration indication.

3. The system of claim 1, wherein said electrical signal processing means includes means for indicating the presence of a gas or gases other than those selected for detection.

4. The system of claim 1, wherein said plurality of semiconductor sensors is fabricated on a single substrate.

5. The system of claim 1, wherein said electrical signal processing means includes means for indicating when the concentration of a selected one of said selected gases or of a combination of said selected gases exceeds a predetermined threshold value.

6. A system according to claim 1, including a plurality of sensor heads each in separate locations dispersed about an environment, one of said heads including said plurality of semiconductor sensors, the others of said heads each consisting of an additional plurality of semiconductor sensors, and means responsive to signals derived from the sensors of said other heads to determine the concentrations of selected sets of gases at each of said other sensor head locations.

7. The system of claim 1, wherein the differences of said response characteristics of at least some of said sensors result from differences in their preparation.

8. The system of claim 1, wherein the differences of said response characteristics of at least some of said sensors result from differences in their operating temperature.

9. The system of claim 1, wherein the differences of said response characteristics of at least some of said sensors result from differences in their combination with a filtering structure.

10. A system of claim 1, wherein at least one of said plurality of sensors is a semiconductor sensor.

11. A system of claim 1, wherein at least one of said plurality of sensors is a solid state sensor.

12. A system of claim 1, wherein at least one of said plurality of sensors is a homogeneous sensor.

13. The system of claim 1, wherein the differences of said response characteristics of at least some of said sensors result from differences in their composition.

14. The system of claim 1, wherein said electrical signal processing means comprises a digital processor.

15. A method for selectively detecting a selected number of gases in an atmosphere, comprising:

deriving from a plurality of sensors a plurality of electrical signals, each of said signals representing the response to said atmosphere of a respectively different one of said sensors, said plurality of sensors being greater or equal in number to the number of selected gases and each having a response characteristic which differs from the response characteristic of each of the other sensors in its response to at least one of the set of selected gases; and electrically processing said plurality of derived signals, for developing respective indications of the concentrations of each of said selected gases as solutions of a set of nonlinear equations, said set of nonlinear equations including terms proportional to products of powers of gas concentrations.

16. A method according to claim 15, wherein each of said equations is of the form:

$$F(R) = 1 + \sum_{i=1}^{L} \left( K_i \prod_{j=1}^{M} [G_j]^{n_{ij}} \right)$$

in which F(R) indicates a known and previously measured function of the response signal R of the particular sensor, j is a counter which indicates the gas type, M is the number of selected gases, $[G_j]$ represent the concentrations of the selected gases; $n_{ij}$ are numerical constants of the particular sensor, $\Sigma$ is the symbol representing summation, i is a counter which distinguishes individual terms in the summation, L is the total number of terms in the summation, $\pi$ is the symbol representing products, and the $K_i$ are previously measured numerical constants of the particular sensor.

* * * * *